United States Patent [19]

Bajgrowicz

[11] Patent Number: 5,703,250

[45] Date of Patent: Dec. 30, 1997

[54] ODORANTS

[75] Inventor: Jerzy A. Bajgrowicz, Zurich, Switzerland

[73] Assignee: Givaudan-Roure (International) SA, Basel, Switzerland

[21] Appl. No.: 706,897

[22] Filed: Sep. 3, 1996

[30] Foreign Application Priority Data

Sep. 11, 1995 [EP] European Pat. Off. ............ 95114200

[51] Int. Cl.[6] .................................................. C07D 319/06
[52] U.S. Cl. .................................................. 549/369; 512/9
[58] Field of Search .................................. 549/369; 512/9

[56] References Cited

U.S. PATENT DOCUMENTS 4,774,225 9/1988 Giraudi .................................. 549/336

FOREIGN PATENT DOCUMENTS 0 043 507 6/1981 European Pat. Off. .

OTHER PUBLICATIONS

G. Buchbauer and C. Lux, *Parfümerie und Kosmetik*, 72, 792–808 (1991).
J.E. Dubois and R. Fellous, *Bull. Soc. Chim. Fr.*, (1963) 786.
M. Perry and Y. Maroni-Barnaud, *Bull. Soc. Chim. Fr.*, (1969) 2372.
V. Dimitrov, K. Kostova, M. Hesse, *Tetrahedron Asymmetry*, 5, (1994) 1891.
V. I. Panseveich-Kolyada, L. N. Falaleeva, *Vestsi Akad. Navuk Belarus. SSR, Ser. Khim. Navuk*, (1970) 106.
B.D. Mookherjee, K.K. Light, I.D. Hill, *Essential Oils*, Eds. B.D. Mookherjee and C.J. Mussinan, Allured Publishing Corp., Wheaton, Illinois, 1981, p. 247.
Isagulyants, V.I., *Zh. Prikl. Khim.*, 41(3):665–8 (1968).
Chemical Abstracts, vol. 69, No. 30, abstract No. 77519h, (1968).

*Primary Examiner*—Amelia Owens
*Attorney, Agent, or Firm*—George W. Johnston; Ellen Ciambrone Coletti; Mark E. Waddell

[57] ABSTRACT

Compounds of the formula:

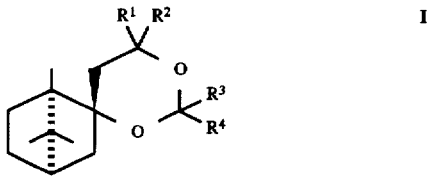

in which $R^1$, $R^2$ represent H or methyl and $R^3$, $R^4$ represent H, $C_{1-4}$ alkyl or $C_{2-4}$ alkenyl; $R^3$ and $R^4$ together can also be butylidene are interesting camphor derivatives. They exhibit valuable odor characteristics.

25 Claims, No Drawings

ODORANTS

FIELD OF THE INVENTION

The invention relates to novel odorants derived from camphor. In particular, these are compounds of the general formula

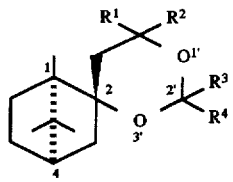

I in which $R^1$, $R^2$ represent, independently, H or methyl and $R^3$, $R^4$ represent, independently, H, $C_{1-4}$ alkyl or $C_{2-4}$-alkenyl; and $R^3$ and $R^4$ together can also be butylidene, thus forming a third spiro ring together with the carbon 2' atom of the dioxane ring.

BACKGROUND

Numerous 5 to 7-membered ring acetals and ketals have been reported as interesting odorant molecules with various olfactory characteristics; for a recent review article see: G. Buchbauer and C. Lux, *Parfümerie und Kosmetik*, 72, 792–808 (1991). Among such structures figure also some spiro[cyclohexane-(1,3-dioxanes)], but they differ significantly from the compounds I by the position of the spiro carbon and by the ring substitution pattern. Perfumery materials structurally related to the tricyclic, camphor derived, compounds I are thus not known.

SUMMARY OF THE INVENTION

The invention relates to novel odorants derived from camphor. In particular, these are compounds of the general formula

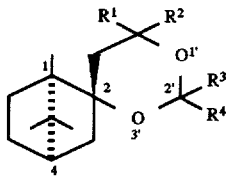

I in which $R^1$, $R^2$ represent, independently, H or methyl and $R^3$, $R^4$ represent, independently, H, $C_{1-4}$ alkyl or $C_{2-4}$-alkenyl; and $R^3$ and $R^4$ together can also be butylidene, thus forming a third spiro ring together with the carbon 2' atom of the dioxane ring.

Suitable $C_{1-4}$-alkyls are methyl, ethyl, propyl, i-propyl, n-butyl and i-butyl, etc.

Preferred are methyl, ethyl and i-propyl.

Examples of $C_{2-4}$-alkenyls are vinyl, allyl, propenyl and i-propenyl, etc.

Preferred are vinyl and i-propenyl.

Methods of making these compounds and compositions employing them are also described herein.

DETAILED DESCRIPTION

The novel compounds I may be obtained from the corresponding diols of the general formula

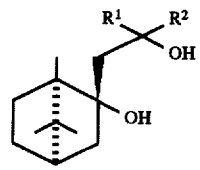

II by direct formation of acetals (or ketals) or by transacetalization, i.e. by reaction of II with a carbonyl compound of the formula

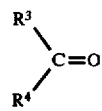

or with its acetal or ketal, i.e. by reaction with

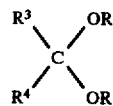

wherein R is preferably $C_{1-4}$ alkyl.

A possible route to these novel compounds I starting from camphor and passing through the compounds II is represented in scheme 1.

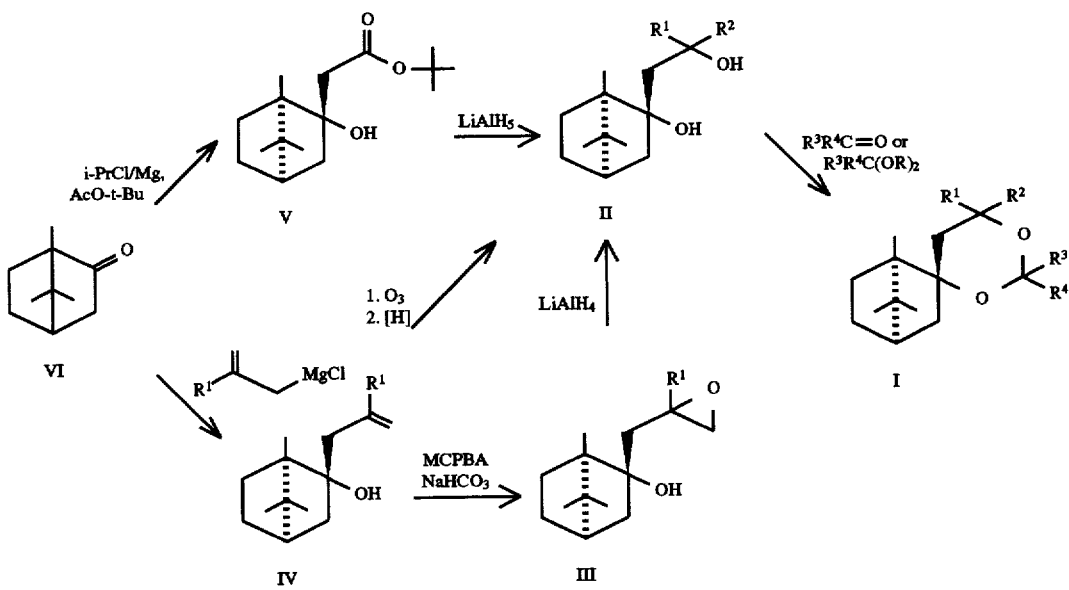

Scheme 1. Spiro[bornyl-2,4'-(1,3-dioxanes)] I

This scheme also shows a preferred route to the intermediate compounds II. This particular route (VI→V→II) is described in the literature: The synthesis of tert-butyl 2-hydroxyborn-2-yl-acetate V and its subsequent LiAlH$_4$ reduction to the unsubstituted diol II (R$^1$, R$^2$=H) was described by J.-E. Dubois and R. Fellous (Bull. Soc. Chim. Fr., (1963) 786) and M. Perry and Y. Maroni-Barnaud (ibid. (1969) 2372). The same diol II and its homologue (R$^1$=H, R$^2$=methyl) were recently obtained by ozonolysis of the homoallylic alcohols IV followed by reduction: V. Dimitrov, K. Kostova, M. Hesse, Tetrahedron Asymmetry, 5, (1994) 1891. The monosubstituted oxirane III was obtained from IV by epoxidation with peracetic acid (V. I. Pansevich-Kolyada, L. N. Falaleeva, Vestsi Akad. Navuk Belarus. SSR, Ser. Khim. Navuk, (1970) 106). Oxiranes III (R$^1$=H and methyl) can preferably by obtained by a metaperbenzoic acid epoxidation of the corresponding homoallylic alcohols IV. They are reduced with lithium aluminum hydride to the diols II (R$^1$, R$^2$=methyl and H,methyl).

As pointed out above, the route from II to the compounds I consists in either a) direct alicyclic acetal (or ketal) formation, or a b) transacetalization.

These reactions are also well known to the skilled artisan per se, namely:

a) acetal (ketal) formation by reacting a diol II with an aldehyde or a ketone and catalyzed with, e.g. Lewis acids, e.g. mineral acids, such as sulfuric or hydrochloric acid, etc. or organic, e.g. sulfonic acids—such as p-toluenesulfonic acid—preferably with—or also without—removal of water through e.g. azeotropic distillation;

b) transacetalization of dialkyl, preferably dimethyl or diethyl acetals or ketals with diols II, even without catalyst, or in the presence of, e.g., a Lewis acid (e.g. a sulfonic acid, e.g. para-toluenesulfonic acid, or a sulfonic acid ion-exchange resin, e.g. Amberlyst 15, optionally in the presence of a lithium halogenide); the reaction can be accelerated by distilling of the volatile alcohol formed from the initial acetal (ketal) used as the reagent.

A suitable temperature range extends from ca. −30° to ca. 150° C.

Both reactions may be carried out with or without solvents. Suitable solvents are the usual aliphatic or aromatic (halogenated) hydrocarbons, ethers and aliphatic esters. Examples are diethyl ether, tetrahydrofuran and methylene chloride.

Transacetalization comes in particular into consideration for R$^1$ and R$^2$ being methyl or H, and both R$^3$ and R$^4$ being alkyl, e.g. methyl, ethyl, propyl or i-propyl, etc.

The compounds of formula I can be isolated and be purified by fractional distillation or flash chromatography.

The details of these methods are illustrated in the Examples. It is understood that modifications concerning the reactants and the reaction conditions are possible.

The general formula I should encompass both the pure isomers and mixtures of configurational, namely optical (see carbons 1, 2, 2', 4, 6') isomers.

In the general formula I, the configuration of carbons 1, 2 and 4 depends on the actual camphor used.

Thus if synthetic, i.e. racemic camphor is used, i.e. a camphor having the configuration 1RS,4RS, the racemates 1RS,2SR,4RS will result, and if the natural product, i.e. the product having the 1R,4R configuration is used, the enantiomers 1R,2S,4R will result.

The configuration of the 2' (dioxane) carbon depends on the reaction conditions of the step II→I: the more stable "thermodynamic" product, i.e. the epimer of the relative configuration 1R*,2S*,2'S'*,4R* - can be obtained with a diastereomeric excess even higher than 95% by prolonged acid catalyzed equilibration of the primary, i.e. "kinetic" epimeric mixture that contains also the 1R*,2S*,2'R*,4R* isomer. In other words, the relative configuration of the carbon atoms of the bornane moiety is always 1R*,2S*,4R*.

It has turned out that the compounds I have very interesting olfactory properties and can be used as odorants, e.g. as perfume ingredients. This use in perfumery is thus also an object of the invention.

The principal olfactory notes of the compounds I are woody and ambery, often accompanied with a camphoraceous, patchouli aspect.

As can be gathered further from the odor description in Table 1 below, the terms woody, earthy, camphoraceous and mossy appear frequently. This is a particular feature of the compounds I: Most of these compounds of the formula I actually exhibit, in fact quite remarkable patchouli side notes, i.e. a note which is particularly looked for, a note which is quite a favorite and represents an important aspect in modern perfume compounding: Patchouli provides a distinct "mother earth" like character (B. D. Mookherjee, K. K. Light, I. D. Hill, in "Essential Oils", Eds. B. D. Mookherjee and C. J. Mussinan, Allured Publishing Corp., Wheaton, Illinois, 1981, p. 247).

The present invention thus also relates to the use of the compounds I, separately or as mixtures, as perfume ingredients for the preparation of any scented products.

The spiro[bornyl-2,4'-(1,3-dioxanes)] I have a woody note with an amber tonality which is extremely advantageous in perfumery. As modern perfumery tends to impose all kind of constraints, especially as regards eliminating the use of amber notes of animal origin, such as ambergris, synthetic products with similar effects in harmony with many other notes such as the woody notes are in demand.

The derivatives I fulfill this requirement.

Their olfactory properties harmonize with a multitude of natural or synthetic products widely used in compositions, for middle and bottom notes, since the compounds I are endowed with very good tenacity.

The compounds I harmonize particularly well with all floral notes, in particular with rose, iris, jasmine, ylang-ylang and narcissus notes. They also harmonize with balsamic or resinous dry-out notes such as styrax, incense, and benzoin, and woody notes, such as oak moss or tree moss, patchouli and vetiver.

They thus provide most distinguished mixtures with a multitude of natural and synthetic raw materials.

Examples are:

natural products, such as, for example, tree moss absolute, basil oil, fruit oils (such as bergamot oil, mandarine oil, etc.), mastix absolute, myrtle oil, palmarosa oil, patchouli oil, petitgrain oil, wormwood oil, lavender oil, rose oil, jasmin oil, ylang-ylang oil or sandalwood oil etc.;

alcohols, such as farnesol, geraniol, linalool, nerol, phenylethyl alcohol, rhodinol, cinnamic alcohol, cis-3-hexenol, menthol, α-terpineol etc.;

aldehydes, such as citral, α-hexyl cinnamaldehyde, hydroxycitronellal, Lilial®, (p-tert.-butyl-α-methyldihydrocinnamaldehyde), methylnonylacetaldehyde, phenylacetaldehyde, anisaldehyde, vanillin etc.;

ketones, such as allylionone, α-ionone, β-ionone, isoraldein (isomethyl-α-ionone), verbenone, nootkatone, geranylacetone etc.;

esters, such as allyl phenoxyacetate, benzyl salicylate, cinnamyl propionate, citronellyl acetate, decyl acetate, dimethylbenzylcarbinyl acetate, ethyl acetoacetate, cis-3-hexenyl isobutyrate, linalyl acetate, methyl dihydrojasmonate, styrallyl acetate, vetiveryl acetate, benzyl acetate, cis-3-hexenyl salicylate, geranyl acetate etc.;

lactones, such as γ-undecalactone, δ-decalactone, pentadecan-15-olide (Exaltolid), 12-oxahexadecanolide (Hibiscolide), etc.;

acetals, such as Viridine®(1,1-dimethoxy-2-phenylethane) etc.;

various components often used in perfumery, such as indole, p-menthane-8-thiol-3-one, methyleugenol, eugenol, anethol etc.

The percentages in which these derivatives are used may vary within wide limits ranging from a few parts per thousand in mass market (cleaning) products up to a few percent in alcoholic extracts for (couture) perfumery. "Overdoses" of up to 20% of these derivatives come also in consideration, and may thus impart very particular effects in combination with synthetic musks.

There is really no restriction regarding the type of formulations and the destination of the actual finished product: eau de cologne, toilet water (eau de toilette), scented water, perfume, cream, shampoo, deodorant, soap, detergent powder, household cleaner, softener, etc. come into consideration.

The spiro[bornyl-2,4'-(1,3-dioxanes)] I integrate into oriental chypres, green and woody florals, floral leathers, fougère tobaccos and fruity aldehydes. They provide, via their olfactory note, exceptional richness and linkage between the dry-out constituents of the compositions by providing more volume, warmth and roundness and augmenting ambery, aromatic, fresh aspects.

Example 1 (Intermediates)

a) (1RS,2SR,4RS)-1,7,7-Trimethyl-2-(2-methyl-oxiranylmethyl)bicyclo[2.2.1]-heptan-2-ol (III)

38.0 g (0.22 mol) of m-chloroperbenzoic acid was added portionwise to a stirred and cooled (ice bath) suspension of 28.7 g (0.14 mol) of (1RS,2SR,4RS)-1,7,7-trimethyl-2-(2-methyl-2-propenyl)bicyclo[2.2.1]heptan-2-ol and 23.1 g (0.27 mol) of sodium bicarbonate in 500 ml of methylene chloride. The temperature was maintained below 20° C. The reaction mixture was stirred at room temperature for an additional 5 hours, filtered and washed with 300 ml of saturated aqueous sodium bicarbonate solution and 300 ml of brine. After drying with $MgSO_4$ and evaporation of the solvent the crude epoxide (30.9 g) was used in the next step without further purification.

b) (1RS,2SR,4RS)-2-(2-Hydroxy-2-methylpropyl),1,7,7-trimethylbicyclo [2.2.1]-heptan-2-ol (II)

A solution of 30.9 g (~0.14 mol) of crude (1RS,2SR,4RS)-1,7,7-trimethyl-2-(2-methyl-oxiranylmethyl)bicyclo[2.2.1]heptan-2-ol in 100 ml of anhydrous diethyl ether was added dropwise to 11.0 g (0.29 mol) of lithium aluminum hydride suspended in 300 ml of the same solvent under reflux, and under nitrogen. The reaction mixture was stirred overnight at room temperature and treated with 60 ml of 2M sodium hydroxide solution. The white precipitate was filtered out, washed with diethyl ether and the combined organic phases were washed with 2×200 ml of water and 200 ml of brine. After drying ($MgSO_4$) and evaporation of solvent the crude (1RS,2SR,4RS)-2-(2-hydroxy-2-methylpropyl)-1,7,7-trimethylbicyclo[2.2.1]heptan-2-ol (29.0 g of white waxy solid; two step yield 92%) was used in the next steps without further purification.

IR (KBr): 3264, 2949, 2874, 1477, 1376, 1326, 1268, 1197, 1174, 975, 881 $cm^{-1}$. $^1H$ NMR (200 MHz; $CDCl_3$): δ0.78-1.77(m,7H); 0.85(s,3H); 0.86(s,3H); 1.09(s,3H); 1.25(s,3H); 1.40(s,3H); 1.92(d,1H,J=14.5); 2.15(dt,1H,J=13;4); 3.46(s,1H exch.); 3.68(s,1H exch.). $^{13}C$ NMR (400 MHz; $CDCl_3$): δ10.06(q), 20.90 (q), 21.43(q), 26.81(t), 28.62(q), 29.66(t), 32.94(q), 45.40(d), 47.91(t), 48.00(s), 48.45(t), 53.68(s), 72.21 (s), 82.12(s). MS (m/z) 226($M^+$, 2), 208(2), 193(7), 152(7), 135(7), 108(46), 95(100), 83(38), 69(36), 59(54), 43(57), 41(49).

Example 2

(1R,2S,4R)-1,2',7,7-Tetramethyl-spiro[bicyclo[2.2.1]heptane-2,4'-(1,3-dioxane)](Ib)

A solution of 9.5 g (47.9 mmol) of (1R,2S,4R)-2-(2-hydroxyethyl)-1,7,7-trimethylbicyclo[2.2.1]heptan-2-ol, 30 ml (0.25 mol) of acetaldehyde diethyl acetal, 0.83 g (9.6 mmol) of lithium bromide and 92 mg (0.5 mmol) of p-toluenesulfonic acid monohydrate in 35 ml of anhydrous THF was stirred under nitrogen for 5 hours, then washed with 3×30 ml of a saturated sodium bicarbonate solution, dried (MgSO$_4$) and evaporated in vacuo. The residue was distilled using a short (5 cm) Vigreux column under 0.09 mm Hg at 72°–79° C. (bath temp. 101°–110° C.) to give 9.8 g of colourless oil (43.7 mmol; yield 91%). It consists of 92% of (1R,2S,2'S, 4R)-1,2',7,7-tetramethyl-spiro[bicyclo-[2.2.1]heptane-2,4'-(1,3-dioxane)] and 8% of the epimeric (1R,2S, 2'R,4R)- 1,2',7,7-tetramethyl-spiro[bicyclo[2.2.1]heptane-2,4'-(1,3-dioxane)]. Overnight stirring of a sample of the reaction mixture gave>98% of the 2'S epimer.

TLC (Merck silica gel 0.25 mm, 60F$_{254}$, MTBE/hexane 1:21) R$_F$=0.40.

The odor description and other physical properties of the product are reported in Tables 1–3.

Example 3

(1R,2S,4R)-2'-Isopropyl-1,7,7-trimethyl-spiro[bicyclo[2.2.1]heptane-2,4'-(1,3-dioxane)](Ii)

A solution of 69.0 g (0.34 mol) of (1R,2S,4R)2-(2-hydroxyethyl)-1,7,7-trimethylbicyclo[2.2.1]heptan-2-ol, 49.0 g (0.68 mol) of isopropanal and 0.65 g (3.4 mmol) of p-toluenesulfonic acid monohydrate in 300 ml of anhydrous THF was stirred at rt under nitrogen for 3.5 hours. After washing with 300 ml of a saturated sodium bicarbonate solution, drying (MgSO$_4$) and evaporation of the solvent in vacuo the residue was rapidly distilled under ~0.1 mm Hg. The main fractions were redistilled using a short (5 cm) Vigreux column under 0.1 mm Hg at 84°–87° C. (bath temp. 137°–138° C.) to give 81.8 g of colourless oil (0.32 mol; yield 95%). It consists of 72% of (1R,2S,2'S,4R)-2'-isopropyl-1,7,7-trimethyl-spiro[bicyclo[2.2.1]heptane-2,4'-(1,3-dioxane)] and 28% of the epimeric (1R, 2S, 2'R ,4R)-2'-isopropyl- 1,7,7-trimethyl-spiro[bicyclo[2.2.1]heptane-2,4'-(1,3-dioxane)].

TLC (Merck silica gel 0.25 mm, 60F$_{254}$, MTBE/hexane 1:4) R$_F$=0.36.

The odor description and other physical properties of the product are reported in Tables 1–3.

TABLE 1

Structure and Odor Characteristics of the novel spiro[bornyl-2,4'-(1,3-dioxanes)] I

| Compound | Absolute config. | R$^1$ | R$^2$ | R$^3$ | R$^4$ | Olfactory description |
|---|---|---|---|---|---|---|
| Ia* | 1RS,2SR,4RS (a) | H | H | H | Me | Woody, ambery,camphor, fruity, earthy/mossy, green, piney |
| Ib** | 1R,2S,4R (b) | H | H | H | Me | Woody, ambery,camphor, animal, earthy/mossy, musky |
| Ic | 1S,2R,4S (b) | H | H | H | Me | Woody, animal,camphor, ambery, earthy/mossy, fruity |
| Id* | 1RS,2SR,4RS | H | H | H | Et | Woody, ambery, fruity, agrestic, earthy/mossy, camphor, green |
| Ie* | 1R,2S,4R | H | H | H | Et | Woody, ambery |
| If | 1RS,2SR,4RS | H | H | H | Vinyl | Woody, ambery, fruity |
| Ig | 1RS,2SR,4RS | H | H | H | Pr | Woody; ambery, camphor, earthy/mossy, leather |
| Ih* | 1RS,2SR,4RS | H | H | H | i-Pr | Woody, ambery, balsamic, fatty, leather |
| Ii** | 1R,2S,4R | H | H | H | i-Pr | Woody, ambery, camphor, earthy/mossy, piney |
| Ij | 1S,2R,4S | H | H | H | i-Pr | Camphor, dry, woody, ambery, earthy |
| Ik* | 1RS,2SR,4RS | H | H | H | CH$_2$CH = CH- | Woody, ambery |
| Il* | 1RS,2SR,4RS | H | H | H | CH$_2$CH = C(CH$_3$)- | Ambery, woody, earthy, camphor |
| Im | 1RS,2SR,4RS | H | H | Me | Me | Camphor, ambery, woody, agrestic, earthy/mossy, leather |
| In | 1R,2S,4R | H | H | Me | Me | Woody, ambery, animal, earthy/mossy, metallic, musky |
| Io | 1RS,2SR,4RS | H | H | Me | Et | Woody, ambery, camphor |
| Ip | 1RS,2SR,4RS | H | H | Et | Et | Ambery, woody, camphor |
| Iq | 1RS,2SR,4RS | H | H | -(CH$_2$)4- | | Woody, ambery, fruity, agrestic, earthy/mossy, camphor |
| Ir | 1R,2S,4R | H | H | -(CH$_2$)4- | | Woody, ambery, fatty, earthy/mossy, tobacco, camphor |
| Is | 1RS,2SR,4RS | H | Me | H | Me | Woody, ambery, camphor, earthy/mossy, metallic, tobacco |
| It | 1RS,2SR,4RS | H | Me | Me | Me | Tobacco, fruity, woody, camphor, earthy, ambery |
| Iu | 1RS,2SR,4RS | Me | Me | H | Me | Woody, dry, earthy, cedar, ambery |

*Preferred compounds
**Most preferred compounds
(a)i.e. two racemates
(b)i.e. two epimers In general, the enantiomers (1R,2S,4R) are somewhat more powerful and "fine".

TABLE 2

Yield and Physical Properties of the Spiro[bornyl-2,4'-)1,3-dioxanes)] I

| Compound | Yield[a] [%] | Method[b] | [a] (c) [° (% in EtOH)] | IR (neat), n [cm$^{-1}$] | MS; m/z (peak abundance[c]) |
|---|---|---|---|---|---|
| Ia | 96 | A | — | 2955, 2873, 1453, 1401, 1266, 1159, 1131, 961 | 224 (M$^+$, 7), 206(4), 180(6), 165(17), 147(9), 137(9), 123(32), 114(49), 109(78), 108(100), 95(92), 81(44), 69(49), 55(57), 41(85) |
| Ib | 91 | A | −44.5 (1.00) | | |
| Ic | 96 | A | +41.0 (1.11) | | |
| Id | 83 | A | — | 2955, 2877, 1466, 1390, 1274, 1165, 1131, 1107, 1034. 979 | 238 (M$^+$, 5), 209(2), 180(5), 165(17), 163(18), 147(8), 128(25), 109(69), 108(94), 95(83), 81(4), 67(41), 57(61), 41(100) |
| Ie | 63 | A | −42.0 (1.07) | | |
| If | 77 | A | — | 2954, 2873, 1460, 1416, 1264, 1147, 1107, 1057, 985, 888 | 236 (M$^+$, 1), 221(4), 179(7), 165(22), 163(16), 147(4), 135(8), 123(16), 109(68), 198(65), 95(47), 81(35), 69(47), 55(92), 41(100) |
| Ig | 73 | A | — | 2958, 2873, 1457, 1383, 1274, 1132, 1010 | 252 (M$^+$, 4), 209(1), 180(5), 165(21), 163(23), 142(17), 123(27), 109(67), 108((100), 95(73), 81(36), 69(43), 55(48), 41(64) |
| Ih | 93 | B | — | 2957, 2874, 1473, 1394, 1264, 1394, 1150, 1111, 1036, 894 | 252 (M$^+$, 4), 209(2), 181(5), 180(5), 165(23), 163(56), 142(119), 123(30), 109(74), 108(100), 95(84), 81(40), 69(40), 55(38), 41 (43) |
| Ii | 95 | B | −33.5 (1.08) | | |
| Ij | 53 | B | +36.5 (1.02) | | |
| Ik | 72 | B | — | 2954, 2872, 1682, 1452, 1389, 1378, 1263, 1127, 1019, 883 | 250 (M$^+$, 1), 235(1), 195(1), 180(7), 165(25), 125(21), 109(57), 108(77), 95(44), 83(48), 69(70), 55(57), 41(100) |
| Il | 74 | B | — | 2954, 2873, 1660, 1453, 1389, 1264, 1113, 1039, 907 | 250 (M$^+$, 1), 235(3), 194(1), 179(11), 165(21), 163(16), 135(9), 123(19), 109(62), 108(76), 95(55), 83(40), 69(56), 55(69), 41(100) |
| Im | 85 | A | — | 2990, 2936, 2872, 1456, 1379, 1273, 1192, 1156, 1108, 979 | 238 (M$^+$, 3), 223(1), 180(16), 165(28), 163(15), 137(9), 128(27), 123(33), 109(67), 108(93), 95(100), 81(38), 69(43), 55(35), 43(51) |
| In | 96 | A | −39.0 (1.07) | | |
| Io | 37 | A | — | 2940, 2873, 1457, 1371, 1269, 1236, 1176, 1109, 1037 | 252 (M$^+$, 3), 237(1), 223(1), 180(16), 165(33), 163(53), 142(21), 142(21), 123(34), 109(66), 108(92), 107(61), 95(100), 81(34), 69(40), 55(43), 43(67), 41(69) |
| Ip | 78 | A | — | 2939, 2877, 1458, 1374, 1275, 1205, 1159, 1109, 987, 925 | 266 (M$^+$, 1), 237(1), 180(9), 165(19), 163(62), 135(8), 123(22), 109(48), 108(73), 107(82), 95(190), 69(46), 57(71), 41(58) |
| Iq | 66 | A | — | 2955, 2872, 1456, 1388, 1332, 1270, 1186, 1126, 1010, 887 | 264 (M$^+$, 3), 180(7), 165(13), 163(54), 147(8), 135(8), 121(19), 108(54), 107(100), 95(73), 79(42), 69(46), 55(80), 41(95) |
| Ir | 54 | A | −49.0 (1.04) | | |
| Is | 84 | A | — | 2951, 2873, 1486, 1449, 1377, 1329, 1154, 1035, 980, 933 | 238 (M$^+$, 1), 194(5), 179(7), 152(4), 136(11), 128(12), 109(47), 108(68), 95(100), 81(60), 69(51), 55(37), 43(67), 41(81) |
| It | 44 | A | — | 2988, 2935, 2874, 1457, 1377, 1244, 1182, 1122, 1005 | 252 (M$^+$, 1), 194(11), 179(7), 177(7), 142(9), 121(11), 109(48), 108(85), 95(100), 81(67), 69(47), 43(74), 41(74) |
| Iu | 50 | A | — | 2951, 2876, 1454, 1399, 1231, 1174, 1113, 1049, 972 | 252 (M$^+$, 1), 208(7), 193(12), 152(11), 137(6), 125(6), 109(48), 108(70), 95(100), 83(44), 81(64), 55(40), 43(52), 41(70) |

[a]Isolated yield of the step II → I;
[b]A-transacetalisation (cf. Example 2), B-direct acetal formation (cf. Example 3);
[c]as percent of base peak (100%)

TABLE 3

$^1$H-NMR Spectra of Spiro[bornyl-2,4'-(1,3-dioxanes)](I)

| Compound | δ(J) of the major diastereomer [a] [ppm(Hz)] |
|---|---|
| Ia,b,c | 0.86–1.78 (m,6H); 0.88 (s,6H); 1.02 (s,3H); 1.11 (dt,1H,J = 13;2); 1.22 (d,3H,J = 5); 1.93 (td,1H,J = 13;5); 2.17 (dt,1H,J = 13;4); 3.80 (ddd,1H,J = 13;11.5;2); 4.03 (ddd,1H,J = 12;5;2); 4.80 (q,1H,J = 5) |
| Id,e | 0.85 (s,3H); 0.86 (s,3H); 0.87 (t,3H,J = 7.5); 0.90–1.78 (m,8H); 1.01 (s,3H); 1.12 (dt,1H,J = 12.5;2); 1.94 (td,1H,J = 13;5); 2.15 (dt,1H,J = 13;3.5); 3.78 (ddd,1H,J = 13;11.5;2.5); 4.03 (ddd,1H,J = 11.5;5.5;2); 4.56 (t,1H,J = 5) |
| If | 0.84–1.80 (m,6H); 0.88 (s,3H); 0.89 (s,3H); 1.02 (s,3H); 1.16 (dt,1H,J = 13;2); 2.01 (td,1H,J = 13;5); 2.21 (dt,1H,J = 13;4); 3.87 (ddd,1H,J = 13;11.5;2.5); 4.10 (ddd,1H,J = 11.5;5;2); 5.08 (d,1H,J = 4); 5.21 (dt,1H,J = 10.5;1.5); 5.40 (dt,1H,J = 17.5;1.5); 5.82 (ddd,1H,J = 17.5;10.5) |
| Ig | 0.83–1.78 (m,13H); 0.85 (s,3H); 1.00 (s,3H); 1.12 (dt,1H,J = 13;2); 1.93 (td,1H,J = 13;5); 2.14 (dt,1H,J = 13;4); 3.78 (ddd,1H,J = 13;11.5;2.5); 4.03 (ddd,1H,J = 11.5;5;2); 4.63 (t,1H,J = 5) |
| Ih,i,j | 0.83–1.78 (m,7H); 0.85 (s,3H); 0.86 (s,3H); 0.88 (d,6H,J = 7); 1.01 (s,3H); 1.11 (dt,1H,J = 13;2); 1.92 (td,1H,J = 13;5); 2.13 (dt,1H,J = 13;3); 3.76 (ddd,1H,J = 13;11.5;2.5); 4.04 (ddd,1H,j = 11.5;5;2); 4.33 (d,1H,J = 5) |

TABLE 3-continued

$^1$H-NMR Spectra of Spiro[bornyl-2,4'-(1,3-dioxanes)](I)

| Compound | δ(J) of the major diastereomer [ppm(Hz)] |
|---|---|
| Ik | 0.85–1.80 (m,6H); 0.87 (s,3H); 0.88 (s,3H); 1.02 (s,3H); 1.14 (dt,1H,J = 13;2); 1.70 (dt,3H,J = 6.5;1); 1.98 (td,1H,J = 13;5.5); 2.20 (dt,1H,J = 13;3.5); 3.85 (ddd,1H,J = 13;11.5;2.5); 4.07 (ddd,1H,J = 11.5;5;2); 5.03 (d,1H,J = 4); 5.47 (ddq,1H,J = 15.5;4;1.5); 5.84 (dqd,1H,J = 15.5;6.5;1) |
| Il | 0.87 (s,3H); 0.87–1.82 (m,6H); 0.88 (s,3H); 1.01 (s,3H); 1.15 (dt,1H,J = 13;2); 1.74 (s,3H); 1.99 (td,1H,J = 13;6); 2.22 (dt,1H,J = 13;3.5); 3.86 (ddd,1H,J = 13;11;2.5); 4.10 (ddd,1H,J = 11.5;5.5;2); 4.91 (broad s,1H); 4.95 (s,1H); 5.11 (broad s,1H) |
| Im,n | 0.81 (s,3H); 0.85 (s,3H); 0.87–1.77 (m,6H); 1.05 (s,3H); 1.15 (dt,1H,J = 13;2.5); 1.29 (s,3H); 1.46 (s,3H); 1.88 (td,1H,H = 13;5.5); 2.35 (dt,1H,J = 12.5;3.5); 3.83 (ddd,1H,J = 12;5.5;2), 4.08 (td,1H,J = 12;2.5) |
| Io | 0.82 (s,3H); 0.85 (s,3H); 0.87–2.03 (m,7H); 0.89 (t,3H,J = 7.5); 1.05 (s,3H); 1.14 (dt,1H,J = 13;2); 1.40 (s,3H); 1.53 (q,2H,J = 7.5); 2.34 (dt,1H,J = 13;3.5); 3.83 (ddd,1H,J = 12;5.5;2); 4.11 (td,1H,J = 12;2.5) |
| Ip | 0.80–2.13 (m,11H); 0.83 (s,3H); 0.83 (t,3H,J = 7); 0.85 (s,3H); 0.86 (t,3H,J = 7); 1.08 (s,3H); 1.15 (dt,1H,J = 13;2); 2.28 (dt,1H,J = 12.5;3.5); 3.79 (ddd,1H,J = 12;5.5;2); 3.99 (td,1H,J = 12;2.5) |
| Iq,r | 0.82 (s,3H); 0.85 (s,3H); 0.88–2.10 (m,15H); 1.05 (s,3H); 1.16 (dt,1H,J = 13;2); 2.33 (dt,1H,J = 13;3.5); 3.85 (ddd,1H,J = 12;5.5;2); 3.94 (td,1H,J = 12;2.5) |
| Is | 0.82–1.77 (m,14H); 0.82 (s,3H); 0.85 (s,3H); 1.00 (s,3H); 2.13 (dt,1H,J = 13;3.5); 3.67–3.84 (m,1H); 4.81 (q,1H,J = 5) |
| It | 0.79 (s,3H); 0.85 (s,3H); 0.90–1.72 (m,8H); 1.05 (s,3H); 1.20 (d,3H,J = 6); 1.30 (s,3H); 1.45 (s,3H); 2.33 (dt,1H,J = 13;4); 4.05 (m,1H) |
| Iu | 0.80–1.77 (m,8H); 0.84 (s,3H); 0.85 (s,3H); 1.01 (s,3H); 1.22 (d,3H,J = 5); 1.33 (s,3H); 2.20 (m,1H); 5.01 (q,1H,J = 5) |

*200 MHz, CDCl$_3$

| Ingredient | parts by weight |
|---|---|
| (1R,2S,4R)-2'-Isopropyl-1,7,7-trimethyl-spiro[bicyclo-[2.2.1]heptane-2,4'-(1,3-dioxane)] (compound Ii) | 50.0 |
| Bornyl acetate | 3.0 |
| Linalyl acetate | 30.0 |
| Ambrettolide | 22.0 |
| Ethylene brassylate | 100.0 |
| Cetalox (Dodecahydro-3a,6,6,9a-tetramethyl-naphtho [2,1-b]furan) | 1.5 |
| Lemon essence Italy | 50.0 |
| Coumarin crist. | 4.0 |
| α-Damascone* | 7.5 |
| β-Damascone* | 3.5 |
| Dihydromyrcenol | 30.0 |
| Dipropylene glycol | 35.5 |
| Fixolide (1,1,2,4,4,7-Hexamethyl-6-acetyl-1,2,3,4-tetrahydro-naphthalene) | 23.0 |
| Galbex 183 (a perfume base; main constituent: Dynascone: 1-([5,5-dimethyl]-cyclohex-1-enyl)-pent-4-en-1-one) | 10.0 |
| Gardenol (Phenyl-methyl-carbinylacetate) | 1.0 |
| Geranium essence | 8.0 |
| Hedione (Methyl dihydrojasmonate) | 60.0 |
| 3-cis-Hexenol* | 1.0 |
| Lavandin oil | 3.0 |
| Linalool synth. | 20.0 |
| Mandarin essence | 15.0 |
| Muscone | 4.5 |
| Pimento berry essence | 2.0 |
| Rose oxide* | 1.0 |
| Thibetolide (Ω-Pentadecalactone) | 8.0 |
| Timberol (1-(2,2,6-Trimethylcyclohexyl)hexan-3-ol) | 5.0 |
| Tropional (α-Methyl-1,3-benzodioxole-5-propanal) | 1.5 |
| | 500.0 |

*10% solution in dipropylene glycol

The novel (1R,2S,4R)-2'-isopropyl-1,7,7-trimethyl-spiro [bicyclo[2.2.1]-heptane-2,4'-(1,3-dioxane)] with its distinct woody, warm, slightly camphoraceous note enriches the composition's floral character with its woody natural note. It also develops the aromatic fresh aspect, gives more volume and imparts an ambery effect to the composition.

b) composition for a fabric softener

| Ingredient | parts by weight |
|---|---|
| (1RS,2SR,4RS)-2'-Isopropyl-1,7,7-trimethyl-spiro[bicyclo-[2.2.1]heptane-2,4'-(1,3-dioxane)] (compound Ih) | 30 |
| Benzyl acetate | 60 |
| Linalyl acetate | 3 |
| Para-tert-butylcyclohexyl acetate | 150 |
| Phenylethyl alcohol | 85 |
| α-Hexyl cinnamic aldehyde | 126 |
| Cyclamen aldehyde | 5 |
| Alismone (2-Heptyl-cyclopentanone) | 1 |
| Anethole | 2 |
| Benzophenone | 12 |
| Cetalox | 1 |
| Citronellol | 15 |
| Cyclal C* (2,4-Dimethyl-3-cyclohexene-1-carbaldehyde) | 8 |
| Dihydromyrcenol | 23 |
| Dipropylene glycol | 140 |
| Ethylvanillin* | 3 |
| Fixolide | 12 |
| cis-3-Hexenyl formate | 1 |
| Galaxolide (1,3,4,6,7,8-Hexahydro-4,6,6,7,8,8-hexamethyl-cyclopenta-[g]-2-benzopyran) 50 DEP (diethyl phthalate) | 60 |
| Galbex 183 | 5 |
| Gardenol | 3 |
| Hedione | 10 |
| 3-cis-Hexenol* | 10 |
| β-Ionone | 8 |
| Isoeugenol | 10 |
| Lavandin grosso essence | 6 |
| Lilial | 120 |
| Linalool synth. | 3 |
| Musk ketone | 5 |
| N 112* (4-(4-Hydroxyphenyl)butan-2-one) | 4 |
| Nerol extra | 4 |
| Nonadienal 1% sol. in triethyl citrate | 3 |
| Allyl oenanthate | 10 |
| Orange essence | 45 |
| Peach pure (γ-Undecalactone) | 5 |
| Phenylethyl phenylacetate | 6 |
| Rosacetol (α-(trichloromethyl)benzyl acetate) | 25 |
| Rosaphen | 25 |
| Rosoflor 2 (Geraniol) | 5 |
| Amyl salicylate | 65 |
| Cyclohexyl salicylate | 45 |
| cis-3-Hexenyl salicylate | 5 |
| Hexenyl salicylate | 110 |
| Tetrahydrolinalool | 6 |
| | 1280 |

*10% solution in dipropylene glycol (1RS,2SR,4RS)-2'-Isopropyl-1,7,7-trimethyl-spiro [bicyclo[2.2.1]heptane-2,4'-(1,3-dioxane)] with its woody, slightly ambery note has been tested in a different application base. As any other compounds of this family it proved to have no masking effect and can be used in a large area of dosage. The addition of only 30 parts per 1280 of this compound enhances the floral spicy character of the composition. It enriches the note with its woody ambery effect.

c) a fine fragrance

| Ingredient | parts by weight |
|---|---|
| (1R,2S,2'S,4R)-1,2',7,7-Tetramethyl-spiro[bicyclo[2.2.1]-heptane-2,4'-(1,3-dioxane)](compound Ib) | 10 |
| Phenylethanol | 15 |
| Methyl anthranilate extra* | 3 |
| Bergamot essence | 80 |
| Calone 1951* | 5 |
| Cetalox | 5 |
| Lemon essence Italy | 10 |
| Cyclogalbanate (Cyclohexyloxyacetic acid 2-propenyl ester) | 2 |
| Dihydromyrcenol | 55 |
| Ethyllinalool | 10 |
| Fixolide | 30 |
| Galaxolide 50 DEP (diethyl phthalate) | 100 |
| Geraniol | 5 |
| Hedione | 200 |
| β-Ionone | 25 |
| Lilial | 15 |
| Linalool | 70 |
| Mandarin essence | 15 |
| Orange essence | 20 |
| Tropional | 25 |
| | 500 |

*10% solution in dipropylene glycol (1R,2S,2'S,4R)-1,2',7,7-Tetramethyl-spiro[bicyclo[2.2.1] heptane-2,4'-(1,3-dioxane)], due to its woody, camphoraceous, ambery notes is widely applicable. In this fine fragrance composition based on hesperidic and floral notes it blends perfectly with these notes enriching the rose aspect. It imparts more sophistication, roundness and volume to the final composition.

I claim:

1. A compound of the formula:

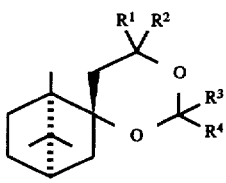

in which $R^1$, $R^2$ represent H or methyl and $R^3$, $R^4$ represent H, $C_{1-4}$ alkyl or $C_{2-4}$ alkenyl and wherein $R^3$ and $R^4$ together can also be butylidene.

2. The compound according to claim 1, wherein $R^3$ and/or $R^4$ are methyl, ethyl, i-propyl, vinyl or i-propenyl.

3. The compound according to claim 1, which is (1RS, 2SR,4RS)-1,2',7,7-tetramethyl-spiro[bicyclo[2.2.1]heptane-2,4'-(1,3-dioxane)].

4. The compound according to claim 1, which is (1R,2S, 4R)-1,2',7,7-tetramethyl-spiro[bicyclo[2.2.1]heptane-2,4'-(1,3-dioxane)].

5. The compound according to claim 1, which is (1S,2R, 4S)-1,2',7,7-tetramethyl-spiro[bicyclo[2.2.1]heptane-2,4'-(1,3-dioxane)].

6. The compound according to claim 1, which is (1RS, 2SR,4RS)-2'-ethyl-1,7,7-trimethyl-spiro[bicyclo[2.2.1] heptane-2,4'-(1,3-dioxane )].

7. The compound according to claim 1, which is (1R,2S, 4R)-2'-ethyl-1,7,7-trimethyl-spiro[bicyclo[2.2.1]heptane-2,4'-(1,3-dioxane)].

8. The compound according to claim 1, which is (1RS, 2SR,4RS)-2'-vinyl-1,7,7-trimethyl-spiro[bicyclo[2.2.1] heptane-2,4'-(1,3-dioxane)].

9. The compound according to claim 1, which is (1RS, 2SR,4RS)-2'-propyl-1,7,7-trimethyl-spiro[bicyclo[2.2.1] heptane-2,4'-(1,3-dioxane)].

10. The compound according to claim 1, which is (1RS, 2SR,4RS)-2'-isopropyl-1,7,7-trimethyl-spiro[bicyclo[2.2.1] heptane-2,4'-(1,3-dioxane)].

11. The compound according to claim 1, which is (1R, 2S,4R)-2'-isopropyl-1,7,7-trimethyl-spiro[bicyclo[2.2.1] heptane-2,4'-(1,3-dioxane)].

12. The compound according to claim 1, which is (1S, 2R,4S)-2'-isopropyl-1,7,7-trimethyl-spiro[bicyclo[2.2.1] heptane-2,4'-(1,3-dioxane)].

13. The compound according to claim 1, which is (1RS, 2SR,4RS)-2'-propenyl-1,7,7-trimethyl-spiro[bicyclo[2.2.1] heptane-2,4'-(1,3-dioxane)].

14. The compound according to claim 1, which is (1RS, 2SR,4RS)-2'-isopropenyl-1,7,7-trimethylospiro[bicyclo [2.2.1]heptane-2,4'-(1,3-dioxane)].

15. The compound according to claim 1, which is (1RS, 2SR,4RS)-1,2',2',7,7-pentamethyl-spiro[bicyclo[2.2.1] heptane-2,4'-(1,3-dioxane)].

16. The compound according to claim 1, which is (1R, 2S,4R)-2',2',7,7-pentamethyl-spiro[bicyclo[2.2.1]heptane-2, 4'-(1,3-dioxane)].

17. The compound according to claim 1, which is (1RS, 2SR,4RS)-2'-ethyl-1,2',7,7-tetramethyl-spiro[bicyclo[2.2.1] heptane-2,4'-(1,3-dioxane)].

18. The compound according to claim 1, which is (1RS, 2SR,4RS)-2',2'-diethyl-1,7,7-trimethyl-spiro[bicyclo[2.2.1] heptane-2,4'-(1,3-dioxane)].

19. The compound according to claim 1, which is (1RS, 2SR,4RS)-1,7,7-trimethyl-dispiro[bicyclo[2.2.1]heptane-2, 4'-(1,3-dioxane)-2',1''-cyclopentane].

20. The compound according to claim 1, which is (1R, 2S,4R)-1,7,7-trimethyl-dispiro[bicyclo[2.2.1]heptane-2,4'-(1,3 -dioxane)-2',1''-cyclopentane].

21. The compound according to claim 1, which is (1RS, 2SR,4RS)-1,2',6',7,7-pentamethyl-spiro[bicyclo[2.2.1] heptane-2,4'-(1,3-dioxane)].

22. The compound according to claim 1, which is (1RS, 2SR,4RS)-1,2',2',6',7,7-hexamethyl-spiro[bicyclo[2.2.1] heptane-2,4'-(1,3-dioxane)].

23. The compound according to claim 1, which is (1RS, 2SR,4RS)-1,2',6',6',7,7-hexamethyl-spiro[bicyclo[2.2.1] heptane-2,4'-(1,3-dioxane)].

24. A process for the manufacture of the compounds of formula

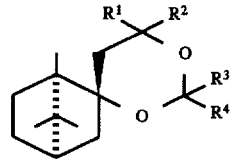

wherein $R^1$, $R^2$ represent H or methyl and $R^3$, $R^4$ represent H, $C_{1-4}$ alkyl or $C_{2-4}$ alkenyl and wherein $R^3$ and $R^4$ together can also be butylidene, comprising reacting a compound of the formula a) with a carbonyl compound of the formula
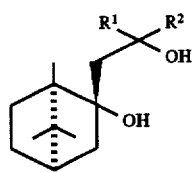
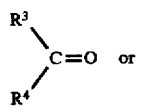
b) its acetal or ketal of the formula
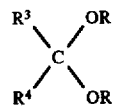
wherein R is preferably $C_{1-4}$ alkyl, under the conditions of acetalisation or ketalisation.
25. An odorant composition containing at least one of the compounds I according to claim 1.
* * * * *

UNITED STATES PATENT AND TRADEMARK OFFICE
CERTIFICATE OF CORRECTION

PATENT NO. : 5,703,250
DATED : December 30, 1997
INVENTOR(S) : Jerzy A. Bajgrowicz It is certified that error appears in the above-identified patent and that said Letters Patent is hereby corrected as shown below:

Column 14, Line 20: Delete: "-trimethylospiro"  Insert: ---trimethyl-spiro--

Column 14, Line 26: Delete: "-2',2',7,7-"  Insert: ---1,2',2',7,7---

Signed and Sealed this

Twenty-first Day of April, 1998

Attest:

BRUCE LEHMAN

Attesting Officer

Commissioner of Patents and Trademarks